(12) United States Patent
Sauer et al.

(10) Patent No.: US 6,891,518 B2
(45) Date of Patent: May 10, 2005

(54) AUGMENTED REALITY VISUALIZATION DEVICE

(75) Inventors: Frank Sauer, Princeton, NJ (US); Ali R. Bani-Hashemi, Walnut Creek, CA (US)

(73) Assignee: Siemens Corporate Research, Inc., Princeton, NJ (US)

(*) Notice: Subject to any disclaimer, the term of this patent is extended or adjusted under 35 U.S.C. 154(b) by 313 days.

(21) Appl. No.: 09/953,679

(22) Filed: Sep. 17, 2001

(65) Prior Publication Data

US 2002/0075201 A1 Jun. 20, 2002

Related U.S. Application Data

(60) Provisional application No. 60/238,253, filed on Oct. 5, 2000.

(51) Int. Cl.$^7$ .................................. G09G 5/00
(52) U.S. Cl. ............... 345/8; 345/7; 345/9; 359/13; 359/630
(58) Field of Search ............. 345/7–9; 359/630–633, 359/638; 382/128–133, 153–154, 162, 171–173, 278, 294

(56) References Cited

U.S. PATENT DOCUMENTS

| | | | | |
|---|---|---|---|---|
| 5,531,227 A | * | 7/1996 | Schneider | 600/425 |
| 5,740,802 A | * | 4/1998 | Nafis et al. | 600/407 |
| 6,204,974 B1 | * | 3/2001 | Spitzer | 359/630 |
| 6,273,896 B1 | * | 8/2001 | Franck et al. | 606/130 |
| 6,351,573 B1 | * | 2/2002 | Schneider | 382/294 |
| 6,402,762 B2 | * | 6/2002 | Hunter et al. | 606/130 |
| 6,546,277 B1 | * | 4/2003 | Franck et al. | 600/426 |

FOREIGN PATENT DOCUMENTS

WO    WO98/38908    * 9/1998

OTHER PUBLICATIONS

Takagi et al., "Development of a Stereo video See–through HMD for AR Systems," IEEE & ACM Int. Symp. On Augmented Reality—ISAR 2000 (Munich, Germany, Oct. 5–6, 2000) pps. 68–77.
Sauer et al., "augmented Workspace: designing an AR testbed" IEEE & ACM Int. Symp. On Augmented—Reality ISAR 2000 (Munich, Germany, Oct. 5–6, 2000) pps. 47–53.
"Video– see–through Head–mounted Displays for Augmented Reality at UNC," http://www.cs.unc.edu/~us/web/headmounts.htm.
Auer et al., "Building a Hybrid Tracking System: Integration of Optical and Magnetic Tracking," htt;://hci.rsc.rockwell.com/iwar/99/WebProceedings/Auer/.
State et al., "Superior Augmented Reality Registration by Integrating Landmark Tracking and Magnetic Tracking," http://www.cs.unc.edu/~us/hybrid.html.
U.S. Appl. No. 09/607,116 entitled "Method and Apparatus for Robust Optical Tracking with Beacon Markers".

* cited by examiner

Primary Examiner—Vijay Shankar

(57) ABSTRACT

A head-mounted display system includes an imaging camera for capturing a view of a workspace located below the head-mounted display system, the imaging camera positioned at a downward pitch angle for capturing an image of the workspace. The system further includes a tracking camera aligned in substantially the same yaw as the imaging camera, the tracking camera for capturing a tracking image including a marker structure, and a display which displays a view of the workspace captured by the imaging camera augmented by a virtual image generated by a processor and registered according to the tracking image.

8 Claims, 4 Drawing Sheets

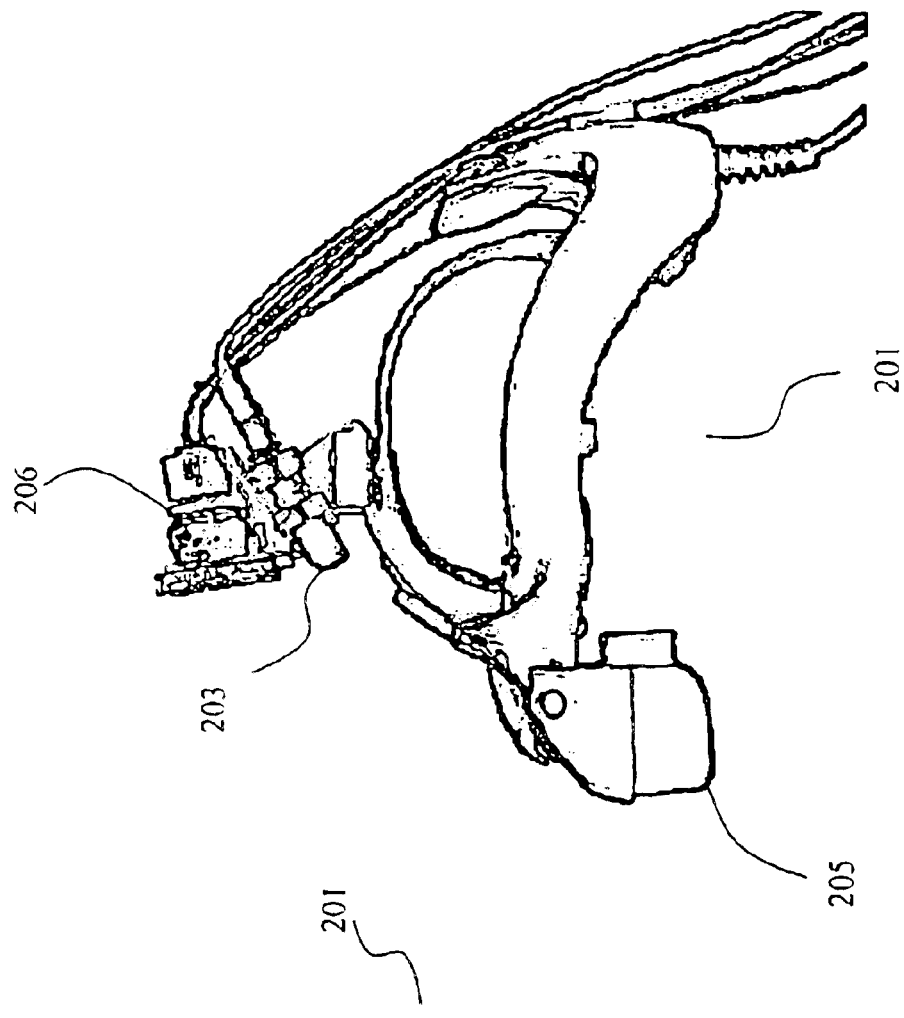
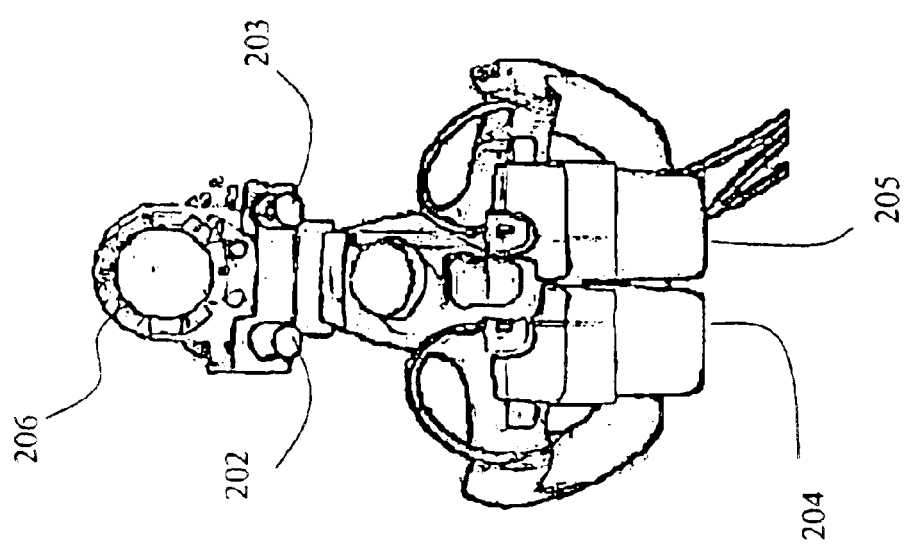
Fig. 2b
Fig. 2a

AUGMENTED REALITY VISUALIZATION DEVICE

This is a non-provisional application claiming the benefit of provisional application Ser. No. 60/238,253 entitled, Intra-Operative-MR Guided Neurosurgery with Augmented Reality Visualization, filed Oct. 5, 2000.

BACKGROUND OF THE INVENTION

1. Field of the Invention

The present invention relates to augmented reality, and more particularly towards a device for augmenting a view with information.

2. Discussion of the Prior Art

Virtual reality is used in many diverse fields, such as kitchen design and military training. Virtual reality emerses a user in a digital environment, where the user's perceptions of sight and sound are manipulated by a computer. While virtual reality provides inexpensive alternatives to building a mock-up of a kitchen or firing live ammunition during an exercise on a battlefield, virtual reality systems lack the sophistication of human perception.

Virtual reality systems have evolved into augmented reality based systems, where a user's perception of a real environment is augmented with information. FIG. 1 is a block diagram illustrating an augmented reality system wherein video images of the environment are combined with computer-generated graphics, according to the prior art. The system includes: a video camera 110; external trackers 112; two dimensional/three dimensional (2D/3D) graphics module 114; an image processing module 116; a pose calculation module 118; a graphics rendering module 120; a video and graphics overlay module 122; and a display 124. As is known, a 3D visual perception may be achieved through use of two cameras and a stereo display.

An augmented reality system can be used to provide guidance to a user, for example, providing information during a surgical procedure. A view of a patient's internal anatomical structures may be overlaid onto a real view of the patient. The internal structures are determined and shown in a graphical representation registered with the view of the real patient.

A head-mounted display (HMD) is a desirable means to display an augmented view to a user. Various HMDs are depicted at http://www.cs.unc.edu/~us/web/headmounts.htm. A HMD allows the user to vary the viewpoint by turning his or her head. However, HMDs are typically cumbersome, especially over longer periods. The weight of a HMD may put a significant strain on a user's neck and back, especially if the user assumes a pose with a tilted head.

The prior art teaches that the difference between the user's natural eye-point and the viewpoint of the video camera is a concern. The prior art proposes designs which attempt to align an imaging camera with the user's line of sight. Designs have been proposed to further include beam combiners to align the optical axis of a camera and a user, e.g., A. Takagai, S. Yamazaki, Y. Saito, and N. Taniguchi, "Development of a Stereo Video-See-Though HMD for AR Systems," IEEE and ACM Int. Symp. On Augmented Reality—ISAR 2000 (Munich, Germany, Oct. 5–6, 2000), pages 68–77. However, these systems do not address the comfort associated with wearing a HMD, particularly when the user assumes a pose with a tilted head.

For registration between the view of the real environment and the augmenting graphics, the user's viewpoint needs to be tracked. In prior art, head-mounted tracking cameras have been used for optical-see-through displays (where the user sees the real environment through a semitransparent display that shows additional graphics), but not for video-see-through displays. An example of an optical-see-through HMD with two head-mounted tracking cameras in conjunction with a magnetic tracker is described by Thomas Auer and Axel Pinz in "Building a Hybrid Tracking System: Integration of Optical and Magnetic Tracking", Proceedings of the 2nd IWAR'99, IEEE Computer Society, (IWAR'99, San Francisco, Oct. 20–21, 1999. In the case of video-see-through HMDs, a method has been proposed which uses the views captured by the imaging cameras for tracking, and a magnetic tracker. See State, Andrei, Gentaro Hirota, David T. Chen, William F. Garrett, and Mark A. Livingston. "Superior Augmented-Reality Registration by Integrating Landmark Tracking and Magnetic Tracking." Proceedings of SIGGRAPH 96 (New Orleans, La., Aug. 4–9, 1996); Computer Graphics Proceedings, Annual Conference Series 1996, ACM SIGGRAPH, pgs. 429–438. However, the tracking capabilities exhibited by the known prior art systems are not suitable in a practical setting for tasks needing precise graphical registration.

Therefore, the need exists for a system and method including a dedicated tracking camera and a downward pitched imaging camera.

SUMMARY OF THE INVENTION

According to an embodiment of the present invention, a head-mounted display (HMD) system is provided. The HMD includes an imaging camera for capturing a view of a workspace located below the head-mounted display system, the imaging camera oriented at a downward pitch angle for capturing an image of the workspace, and a display for displaying a view of the workspace captured by the imaging camera. The pitch angle is greater than about 25 degrees down angle.

The HMD system includes two imaging cameras for capturing a stereoscopic view of the workspace, wherein the display is stereoscopic. The HMD system further includes a tracking camera for capturing a field of view including a marker structure.

The marker structure is adjacent to a workspace. The marker structure frames a workspace. The marker structure includes a plurality of light emitting diodes, visible to the tracking camera. The marker structure comprises a plurality of retro-reflectors and the tracking camera further comprises a light source.

The HMD system includes a head-mounted tracking camera having a forward-looking orientation. The tracking camera is attached to the imaging camera at a fixed orientation. The tracking camera includes a field of view wider than a field of view of the imaging camera. The tracking camera further comprises a visual-cut, infrared-pass filter.

The HMD system includes a plurality of markers visible to a tracking camera, wherein the tracking camera is positioned with a view including the head-mounted-display.

The pitch angle of the imaging camera facilitates a substantially erect head posture.

According to an embodiment of the present invention, a HMD system is provided. The system includes an imaging camera for capturing a view of a workspace located below the head-mounted display system, the imaging camera for capturing an image of the workspace. The system further includes a tracking camera aligned in substantially the same yaw as the imaging camera, the tracking camera for capturing a tracking image including a marker structure, and a display which displays a view of the workspace captured by the imaging camera augmented by a virtual image generated by a processor and registered according to the tracking image.

The imaging camera is oriented at a downward pitch angle. The tracking camera is oriented having a forward-looking view.

According to one embodiment of the present invention, a HMD system is provided. The HMD system includes a pair of imaging cameras for capturing a stereoscopic view of a workspace and a tracking camera for capturing a field of view including a marker structure, the tracking camera having a fixed position and orientation relative to the pair of imaging cameras. The HMD system further includes a display for displaying the stereoscopic view of the workspace captured by the pair of imaging cameras and augmented with a computer graphic according to a position and orientation of the imaging cameras relative to the workspace, and a processor for determining the position and orientation of the imaging cameras relative to the workspace based on the location of the marker structure within the field of view of the tracking camera.

The pair of imaging cameras is oriented having a downward pitch angle greater than about 25 degrees. The downward pitch angle of the pair of imaging cameras facilitates a substantially erect head posture. The tracking camera is fixed having a forward-looking view.

The HMD system further comprises a plurality of tracking cameras for capturing a plurality of fields of view, the tracking cameras having fixed positions and orientations relative to the pair of imaging cameras.

BRIEF DESCRIPTION OF THE DRAWINGS

Preferred embodiments of the present invention will be described below in more detail, with reference to the accompanying drawings:

FIG. 2a is a frontal view of a stereo video-see-through head-mounted display according to an embodiment of the present invention;

FIG. 2b is a side view of a stereo video-see-through head-mounted display according to an embodiment of the present invention;

DETAILED DESCRIPTION OF PREFERRED EMBODIMENTS

Figure 1:
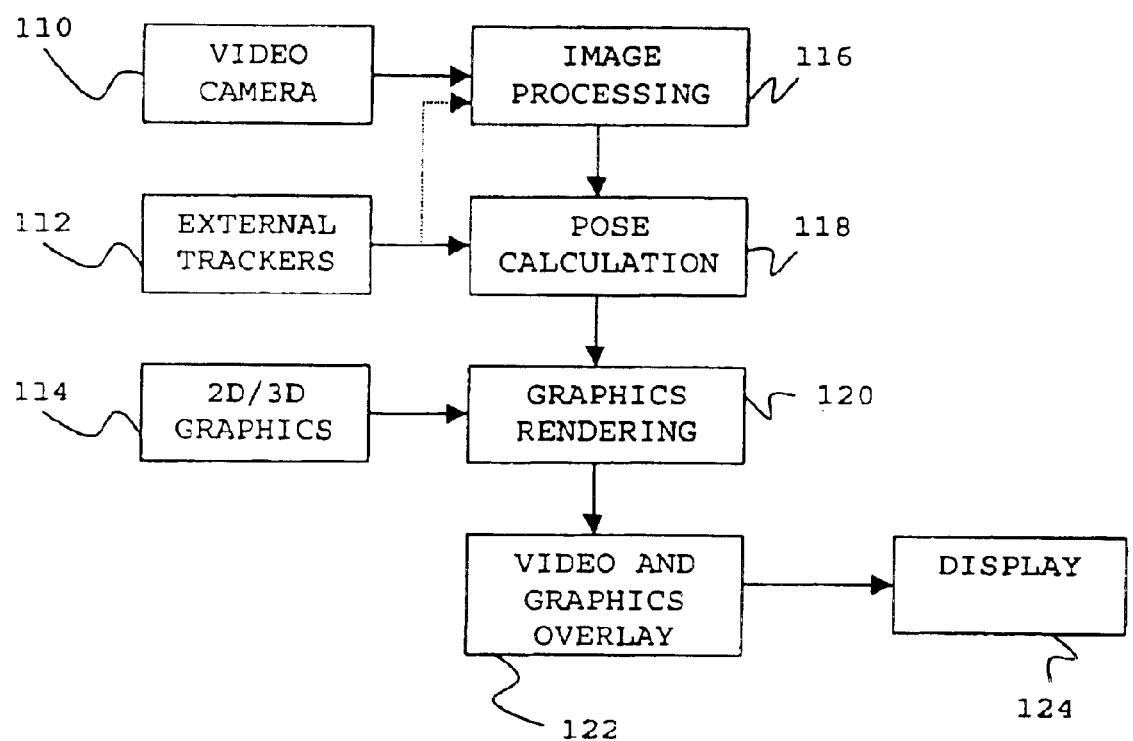
FIG. 1 is a block diagram illustrating an augmented reality system wherein video images of the real world are combined with computer-generated graphics, according to the prior art.

The present invention presents a system for augmenting reality. A stereo video-see-through head-mounted display (HMD) is provided including a pair of imaging cameras attached to the HMD. The HMD displays synchronized real and virtual images. The calibration of the HMD is based on captured images and can be performed objectively by a computer processor. The video-see-through HMD is reliable, for example, a shift of a video-see-through HMD with respect to a user's head does not influence the registration (alignment) of an augmented view. Further, the augmented view may be shared with other users viewing, for example, traditional video monitors.

The imaging cameras capture a stereoscopic view of a scene. The stereoscopic view is augmented with additional information and provided to a user in real time. The additional information can include, for example, text, audio, video, and still images. For example, in a surgical workspace, a surgeon may be provided with a view of a patient including, inter alia, the view of the patient and an overlay generated by a processor. The overlay may include a view of the patient's internal anatomical structures as determined, for example, during a Computerized Axial Tomography (CAT) scan, or by Magnetic Resonance Imaging (MRI). Another example of an overlay can include a textual view of the patient's medical and family history. These overlays may be displayed in real-time.

The augmented view includes the real view overlaid with an additional virtual view. The real view is provided as video images. The virtual view is derived from a processor and stored information, for example, images.

The real view and the virtual view may be blended. For example, the virtual view is provided as a transparency over the real view of the workspace. Registration between the real view and the virtual view aligns the real and virtual views. Registration of the virtual view includes, inter alia, position, orientation, scale, perspective, and the internal camera parameters for each camera. Preferably, these internal camera parameters are determined in a prior camera calibration procedure. The registered virtual view is aligned with the real image of the workspace in real time.

Graphics in the virtual view may be anchored to a real image of an object in a workspace. To anchor an image, the position and orientation of the imaging cameras with respect to the object, and the orientation of the object, need to be determined. For anchoring, the system needs to know the relationship between two coordinate systems, a camera coordinate system attached to the camera, and a coordinate system attached to the object. Tracking denotes the process of monitoring the relationship between these coordinate systems.

According to an embodiment of the present invention, a tracking camera is rigidly attached to the imaging cameras. The tracking camera is oriented having a forward-looking view. In the forward-looking orientation, the tracking camera looks in approximately the same direction as the imaging cameras, with tracking camera's pitch or up-down orientation and yaw or left-right orientation differing from the imaging cameras' pitch and yaw by no more than about 35 degrees. The tracking camera may have a larger field-of-view than the imaging cameras. The tracking camera is used to locate markers. Markers may be adjacent to or preferably around the workspace. Based on 3D marker coordinates in a workspace coordinate system, the internal parameters of the tracking camera, and the measurement of the 2D coordinates of the markers in the tracking camera's image, the pose of the tracking camera with respect to the workspace coordinate system can be determined.

The tracking camera, located on the HMD, optimizes the perceived accuracy of the augmentation. Movements along the optical axis may be tracked with a lower accuracy than transverse movement. However, a depth error of a virtual object's position is less perceptible than a lateral error. For a forward-looking tracking camera, the tracking camera detects at least what the user sees. What the tracking camera does not detect, the user may not be able to see.

Referring to FIGS. 2a and 2b, the system includes a video-see-through HMD 201. The HMD includes a pair of imaging cameras 202–203 which capture a stereoscopic view of the real scene and a pair of displays 204–205 which display the view (a real view or an augmented real view) stereoscopically. According to an embodiment of the present invention, the imaging cameras are pitched downward. Because the imaging cameras are pitched downward, the user can view a downward workspace while maintaining a substantially upright head posture, looking ahead into the displays. The angle between the optical axes of the imaging cameras and the viewing direction of the user may be between about 0 degrees and about 60 degrees. According to a preferred embodiment of the present invention, the pitch angle is greater than about 25 degrees down angle.

For stereoscopic vision, two imaging cameras may be used, though the number of cameras may vary. The imaging cameras are spaced apart by a distance that approximates an average interpupillary distance. In one example, the imaging cameras are spaced apart by 6.5 cm. Preferably, the optical axes of the imaging cameras converge at about an object of interest. The vertex or point of convergence corresponds to the distance of optimal overlap of the stereo images. For example, in a surgical theater, a desirable vertex may be located about at the patient or about 60 cm from the imaging cameras. For fixed-focus cameras, the focal length of the imaging cameras may be set to the same distance.

According to an embodiment of the present invention, imaging cameras capable of zooming and/or auto-focus may be implemented. Thus, the magnification of an object of interest may be varied. With auto-focus, the user's view is in focus over varying distances. The system monitors the zoom and focus of the imaging cameras using, for example, encoders attached to the imaging cameras, and calibrates the alignment and zoom of the augmented view accordingly.

The system includes a tracking camera 206 rigidly attached to the imaging cameras 202–203. The relationship between the tracking camera 206 and the imaging cameras 202–203 is known. The relationship is used to determine the position and orientation (collectively referred to as pose information) of the imaging cameras 202–203 based on the tracking camera 206.

The invention defines a common frame of reference or a common coordinate system for monitoring the relationship between the 2D images and the 3D data. The common coordinate system is defined by markers. The markers are preferably placed around the workspace. The workspace includes the area where the user performs work. Accordingly, the markers will not interfere with the user, and the user will not interrupt the line of sight between markers and tracking camera.

The system can relate 3D volume or surface data and 3D camera poses to the common coordinate system. The system relates the pose of the tracking camera 206 to the imaging cameras 202–203 based on prior system calibration to determine the relationship between the tracking camera 206 and the imaging cameras 202–203. The tracking camera 206 and processor use the markers to determine the pose of the imaging cameras 202–203 within the common coordinate system.

Figure 4:
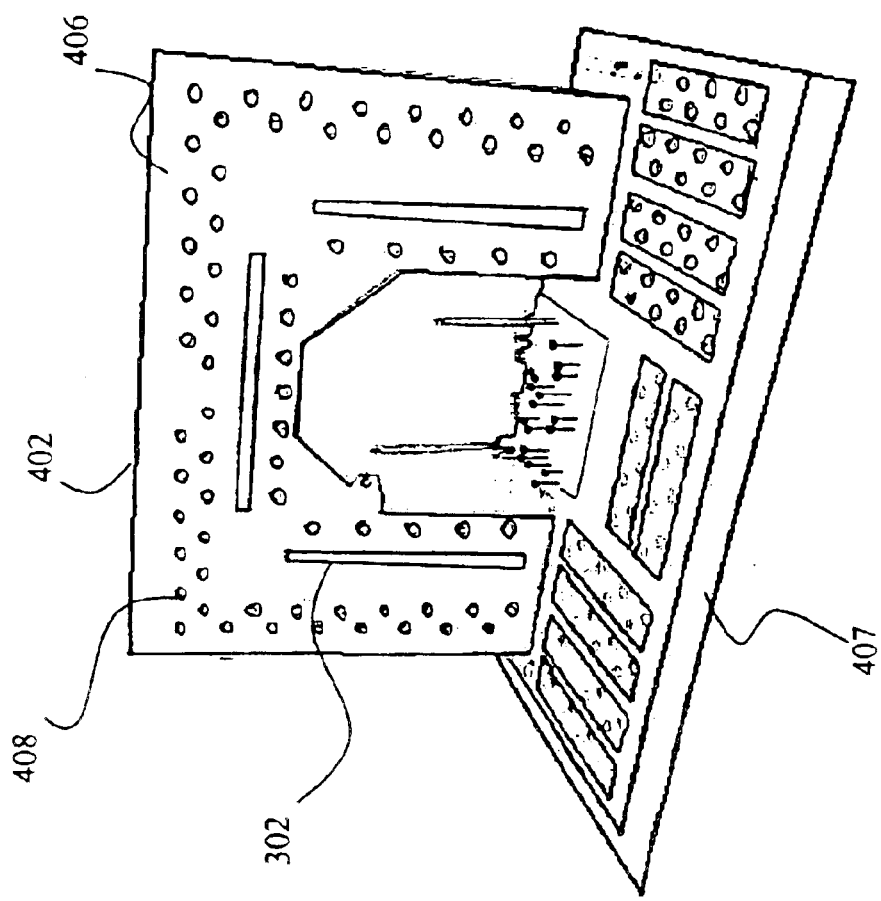
FIG. 4 is an illustration of a calibration object according to an embodiment of the present invention.

Calibration of the cameras is needed for the registration between real objects and virtual objects. According to an embodiment of the present invention, a method of calibration uses a calibration object or workspace frame (e.g., a marker structure). FIG. 4 shows an example of a calibration object 402 including a plurality of disc markers (e.g., 404) on various planes (e.g., 406, 407) wherein the geometric relationships between markers are known. Markers may vary in shape and size. For an example of a calibration object see F. Sauer, F. Wenzel, S. Vogt, Y. Tao, Y. Genc, and A. Bani-Hashemi, "Augmented Workspace: Designing an AR Testbed," IEEE and ACM Int. Symp. On Augmented Reality—ISAR 2000 (Munich, Germany, Oct. 5–6, 2000), pages 47–53.

The camera calibration is based on known 2D/3D point correspondences between the markers within tracking camera images and the known 3D marker coordinates. The 2D marker positions may be determined from the tracking camera images. Further, camera calibration includes determining internal parameters and external parameters of the cameras. The external parameters or pose, includes the position of the cameras relative to six degrees of freedom (e.g., translation and rotation). For a given relationship between the rigidly coupled imaging and tracking cameras, the pose of the imaging cameras 202–203 may be deduced from the pose of the tracking camera 206.

Real-time pose determination, similar to the initial system calibration, is preferably based on the 2D/3D point correspondences. The external camera parameters (camera pose) can then be determined based on the known internal camera parameters and point correspondence list. In a preferred embodiment, at least four markers are used to calculate the tracking camera's pose. Additional markers may reduce any noise in the pose calculation and achieve a better accuracy.

The tracking camera may operate in the infrared wavelength region of electromagnetic spectrum to obtain images including markers. The visual wavelengths may be eliminated with a visible-cut, infrared-pass optical filter. The markers may be active light sources, including for example, infrared light emitting diodes, or passive retro-reflectors used in conjunction with an infrared illuminator. The illuminator may be placed close to the optical axis of the tracking camera, for example, around the tracking camera's lens.

Figures 3A, 3B:
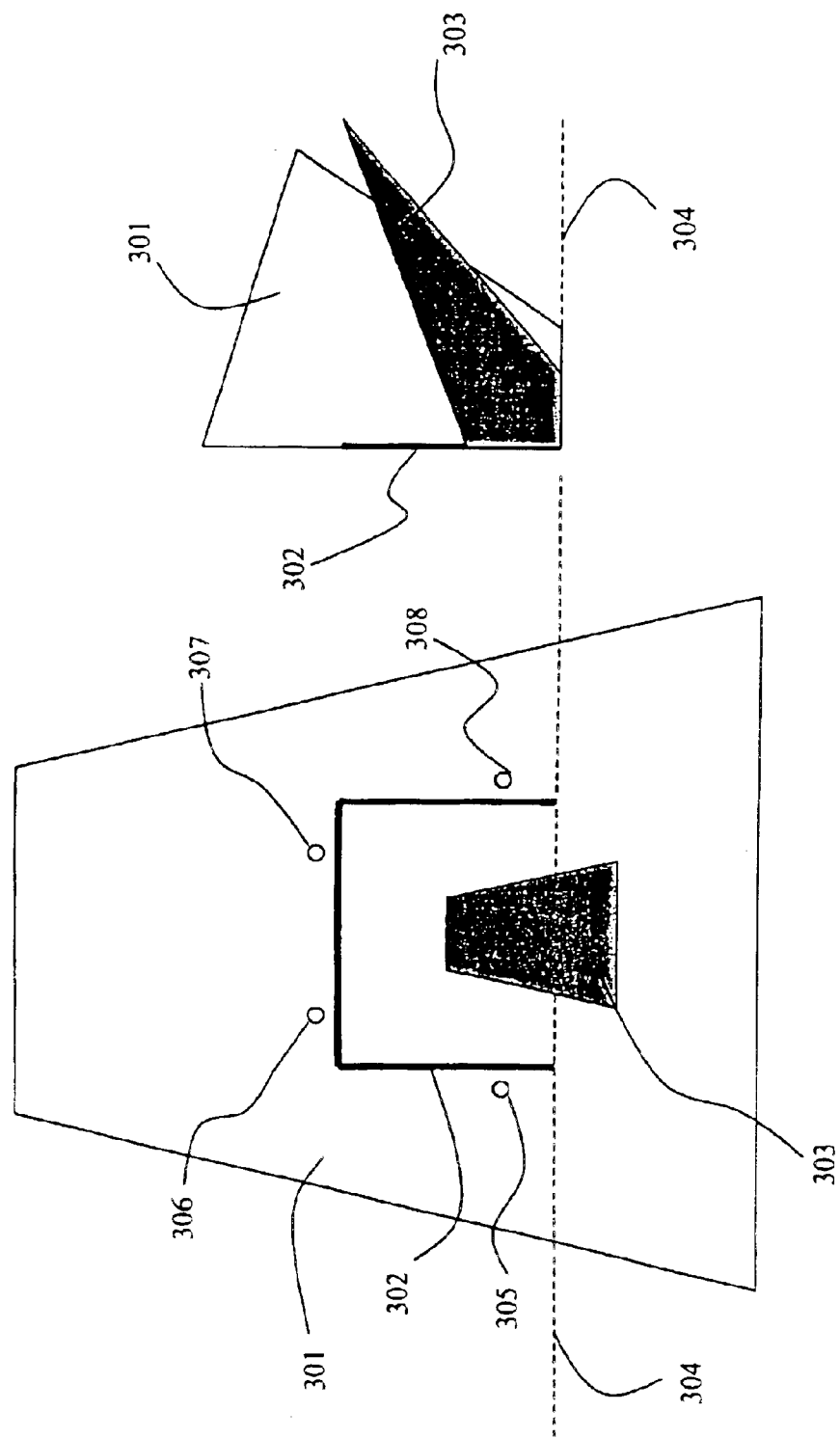
FIG. 3a is an illustration of the fields of view as captured by an imaging camera and a tracking camera according to an embodiment of the present invention.
FIG. 3b is an illustration of the fields of view of an imaging camera and a tracking camera as seen from the side, corresponding to the view of the head-mounted display as seen in FIG. 2b.

Preferably, the tracking camera 206 is a wide-angle camera, rigidly attached to the imaging cameras 202–203. The tracking camera may be, for example, a 3.8 mm fish-eye camera with a view including 170 degrees for a ⅔ inch CCD chip. The tracking camera 206 has substantially the same yaw as the imaging cameras. According to an embodiment of the present invention, the downward pitch angle between the optical axes of the tracking and imaging cameras may be less than about 25 degrees, though the angle may be larger for different workspace configurations. The downward pitch angle of the imaging cameras can be between about 25 and about 45 degrees from horizontal, though the angle may be larger or smaller for different workspace configurations. Referring to FIGS. 3a and 3b, the field of view of the tracking camera 301 includes four non-collinear marker points 305–308 on the workspace frame 402. The markers define a common coordinate system for the workspace. The markers are used to determine the pose of the tracking camera in the common coordinate system. Knowing the relationship between the tracking and imaging cameras, the pose of imaging cameras can be determined. Therefore, augmenting graphics objects may be rendered or registered into stereo video images from the video viewpoints of the imaging cameras. The graphics can appear anchored in the augmented scene. The imaging camera's field of view 303 can also be determined. A table level 304 is shown as a line of reference between FIGS. 3a and 3b.

According to an embodiment of the present invention, the workspace frame 402 includes guidelines 302. The method processes each image frame individually, without relying on information from previous image frames. Thus, the present invention does not depend on slow marker or head movement to locate a marker from one image frame to the next. Rather, the guidelines 302 limit the method's search for markers, within the tracking camera's view, to a defined area. Systems and methods for using guidelines are described in the commonly assigned and co-pending U.S. patent application Ser. No. 09/607,116, entitled "Method and Apparatus for Robust Optical Tracking with Beacon Markers," incorporated herein by reference in its entirety. The markers are used for precise tracking. Thus, a marker need not be in the vicinity of its previous position in a previous image frame.

The imaging cameras may be pitched at an angle. The angle of the imaging cameras preferably enables a user to maintain a comfortable and relaxed posture. For example, a surgeon may prefer to pitch the imaging cameras downward at a particular angle, with a view of a patient. Thus, the surgeons head and neck posture can remain substantially upright throughout the procedure. Additional tracking cameras can cover a larger field of view than a single tracking camera. Overlapping views may allow stereo triangulation for identifying individual markers and increase the accuracy of the pose determination.

According to an embodiment of the present invention, one or more tracking cameras may be mounted in the environment, preferably close to the workspace. Tracking markers placed on the HMD, rigidly coupled to the imaging cameras, may be used to determine pose information.

The processor renders, in real time, an augmented stereo view. The processor receives video images from the imaging cameras, video images for determining pose information from the tracking camera, and stored volume and/or 3D surface data relating to the virtual view. The virtual view is rendered according to the camera pose information, determined by the processor, and blended with the corresponding video images. The augmented images can be displayed stereoscopically.

A user may be provided with a suite of tools, for example, allowing the user to enhance the views with color, or text, the user may select objects in the workspace, or include graphical objects as guides.

Having described embodiments for a head-mounted augmented reality system, it is noted that modifications and variations can be made by persons skilled in the art in light of the above teachings. It is therefore to be understood that changes may be made in the particular embodiments of the invention disclosed which are within the scope and spirit of the invention as defined by the appended claims. Having thus described the invention with the details and particularity required by the patent laws, what is claims and desired protected by Letters Patent is set forth in the appended claims.

What is claimed is:

1. A head-mounted display system comprising:
   a pair of imaging cameras for capturing a stereoscopic view of a workspace, the pair of imaging cameras being oriented at a downward pitch angle greater than 25 degrees with respect to a user's line of sight;
   a tracking camera for capturing a field of view including a marker structure, the tracking camera having a fixed position and forward-looking orientation relative to the pair of imaging cameras, the tracking camera having a field of view wider than a field of view of the imaging camera;
   a display for displaying the stereoscopic view of the workspace captured by the pair of imaging cameras and augmented with a computer graphic according to a position and orientation of the imaging cameras relative to the workspace; and
   a processor for determining the position and orientation of the imaging cameras relative to the workspace based on the location of the marker structure in the field of view captured by the tracking camera.

2. The system of claim 1, wherein the marker structure is adjacent to a workspace.

3. The system of claim 1, wherein the marker structure includes a plurality of light emitting diodes, visible to the tracking camera.

4. The system of claim 1, wherein the marker structure comprises a plurality of retro-reflectors and the tracking camera further comprises a light source.

5. The system of claim 1, wherein the tracking camera further comprises a visual-cut, infrared-pass filter.

6. The system of claim 1, wherein the pair of imaging cameras is oriented at a downward pitch angle for facilitating a substantially erect head posture.

7. The system of claim 1, wherein the marker structure frames a workspace.

8. The system of claim 1, further comprising a plurality of tracking cameras for capturing a plurality of fields of view, the tracking cameras having fixed positions and orientation relative to the pair of imaging cameras.

* * * * *